(12) United States Patent
Takachi

(10) Patent No.: US 6,758,110 B1
(45) Date of Patent: Jul. 6, 2004

(54) MECHANICAL LOCK MECHANISM AND INJECTOR HEAD USING THE MECHANISM

(75) Inventor: Ken Takachi, 6-59, Koyoenhinode-cho, Nishinomiya-shi, Hyogo 662-0014 (JP)

(73) Assignee: Ken Takachi, Hyogo (JP)

( * ) Notice: Subject to any disclaimer, the term of this patent is extended or adjusted under 35 U.S.C. 154(b) by 0 days.

(21) Appl. No.: 09/720,596

(22) PCT Filed: Apr. 24, 2000

(86) PCT No.: PCT/JP00/02694

§ 371 (c)(1),
(2), (4) Date: Dec. 26, 2000

(87) PCT Pub. No.: WO00/64512

PCT Pub. Date: Nov. 2, 2000

(30) Foreign Application Priority Data

Apr. 26, 1999 (JP) .......................................... 11-117918

(51) Int. Cl.⁷ ............................................. A61M 5/145
(52) U.S. Cl. ....................... 74/89.39; 74/89.37; 600/432
(58) Field of Search ............................. 74/89.37, 89.39; 192/139, 141, 143, 223.2; 604/155; 600/432; 222/310

(56) References Cited

U.S. PATENT DOCUMENTS

| | | | | |
|---|---|---|---|---|
| 2,283,476 A | * | 5/1942 | Waibel | ........................ 192/141 |
| 2,854,113 A | * | 9/1958 | Hallden | ........................ 192/141 |
| 2,986,023 A | * | 5/1961 | Eickoff | ........................ 464/160 |
| 3,593,829 A | * | 7/1971 | Williams | ........................ 192/141 |
| 3,631,847 A |   | 1/1972 | Hobbs, II | |
| 4,157,716 A |   | 6/1979 | Rüegg | |
| 5,244,461 A |   | 9/1993 | Derlien | |
| 5,614,778 A | * | 3/1997 | Terao et al. | ........................ 310/80 |
| 5,968,015 A |   | 10/1999 | Yamamoto | |

FOREIGN PATENT DOCUMENTS

| | | |
|---|---|---|
| EP | 0 354 852 | 2/1990 |
| FR | 2 281 665 | 3/1976 |
| JP | 48-31890 | 4/1973 |
| JP | 56-160548 | 11/1981 |
| JP | 60-104696 | 6/1985 |
| JP | 3-117758 | * 5/1991 |
| JP | 5-42219 | 2/1993 |
| JP | 5-289763 | 11/1993 |
| JP | 10-244002 | 9/1998 |

* cited by examiner

Primary Examiner—William C. Joyce
(74) Attorney, Agent, or Firm—McDermott, Will & Emery

(57) ABSTRACT

This injector head 1000 comprises a plunger 20 capable of reciprocating in a direction of movement of a piston 1a in a syringe 1, a plunger drive 500 for converting rotary motion of a plunger motor 2 to linear motion in order to supply reciprocation to this plunger 20, and a safety device 600 as safety means for restraining rotation of a rotary shaft 2a of the plunger motor 2 when the plunger 20 moves beyond a predetermined position. Thus, it is possible to provide a medical injector head attaining miniaturization and simplification of the apparatus while keeping a mechanical safety mechanism.

9 Claims, 10 Drawing Sheets

MECHANICAL LOCK MECHANISM AND INJECTOR HEAD USING THE MECHANISM

TECHNICAL FIELD

The present invention relates to a mechanical locking mechanism and an injector head employing the mechanism, and more specifically, it relates to an improvement of a structure for attaining miniaturization of a mechanical locking mechanism and an injector head employing the mechanism.

BACKGROUND TECHNIQUE

In recent years, various ones are developed as apparatuses testing functions of a human body. There is a circulatory organ X-ray diagnostic apparatus for diagnosing the functions of circulatory organs of a human body as one of these apparatuses. In this circulatory organ X-ray diagnostic apparatus, an injector head for injecting a contrast medium into a patient is employed.

According to the structure of a general injector head, a safety device for mechanically limiting movement of a plunger for moving a piston in a syringe filled with a contrast medium is provided. When providing this safety device on the injector head, the injector head tends to be large-sized.

In an injector head disclosed in Japanese Patent Laying-Open No. 10-244002, on the other hand, a structure attaining miniaturization of the injector head by providing a mechanical stopper arranged coaxially with a plunger for sliding in the axial direction of the plunger is employed.

According to the structure of the aforementioned conventional injector head, however, the structure of mechanically stopping the plunger having the largest torque itself with the mechanical stopper is employed. When mechanically stopping the plunger with the mechanical stopper, therefore, stress applied to the plunger, the mechanical stopper and other components increases.

Consequently, it forms the design basis to withstand this stress in strength design of the components such as the plunger subjected to application of the stress, and size increase of these components cannot be avoided. Consequently, there is a limit in the point of attaining miniaturization of the injector head.

Accordingly, an object of the present invention is to attain further miniaturization and simplification of a mechanical locking mechanism and an injector head employing the mechanism while keeping a mechanical safety mechanism of the mechanical locking mechanism and the injector head employing the mechanism.

DISCLOSURE OF THE INVENTION

In a mechanical locking mechanism based on the present invention, it is a mechanical locking mechanism for stopping a movable shaft capable of reciprocation, and comprises a movable shaft drive for converting rotary motion of a drive to motion of a prescribed direction in order to supply reciprocation to the aforementioned movable shaft and a safety device for restraining rotation of a rotary shaft of the aforementioned drive by a mechanical operation when the aforementioned movable shaft moves beyond a predetermined position.

Thus, torque caused on the rotary shaft of the drive is by far smaller than torque caused on the movable shaft, and hence it is possible to stop movement of the movable shaft with small force by restraining rotation of the rotary shaft of the drive by a mechanical operation. Therefore, stress applied to components forming the safety device also reduces and it is possible to attain miniaturization of these components and miniaturization of the mechanical locking mechanism following the same.

In order to execute the aforementioned invention in a preferable state, the following structure is employed: The aforementioned safety device includes a locking device provided in the vicinity of the aforementioned rotary shaft to be capable of restraining rotation of the rotary shaft of the aforementioned drive and a trigger device mechanically operating the aforementioned locking device so that the aforementioned locking device restrains the aforementioned rotary shaft when the aforementioned movable shaft moves beyond the predetermined position.

Further, the aforementioned locking device is provided to be capable of selecting a first position restraining rotation of the aforementioned rotary shaft and a second position liberating rotation of the said rotary shaft, and the aforementioned trigger device includes a detection mechanism for mechanically detecting a moving end of the aforementioned movable shaft and a link mechanism setting the aforementioned locking device on the first position by the aforementioned detection mechanism when the aforementioned movable shaft moves beyond the predetermined position.

This structure makes detection of the position of the movable shaft implementable by the detection mechanism consisting of only a mechanical structure, whereby safety of the operation of the mechanical locking mechanism can be attained regardless of a failure of electric control.

In an injector head based on the present invention, it is an injector head provided therein with a syringe filled with a contrast medium, and comprises a plunger capable of reciprocating in a direction of movement of a piston in the aforementioned syringe, a plunger drive for converting rotary motion of a motor to linear motion in order to supply reciprocation to the aforementioned plunger and a safety device for restraining rotation of a rotary shaft of the aforementioned motor by a mechanical operation when the aforementioned plunger moves beyond a predetermined position.

Thus, torque caused on the rotary shaft of the motor is by far smaller than torque caused on the plunger, and hence it is possible to stop movement of the plunger with small force by restraining rotation of the rotary shaft of the motor by a mechanical operation. Therefore, stress applied to components forming the safety device also reduces and it is possible to attain miniaturization of these components and miniaturization of the injector head following the same.

In order to execute the aforementioned invention in a preferable state, the following structure is employed: The aforementioned safety device includes a locking device provided in the vicinity of the aforementioned rotary shaft to be capable of restraining rotation of the rotary shaft of the aforementioned motor and a trigger device mechanically operating the aforementioned locking device so that the aforementioned locking device restrains the aforementioned rotary shaft when the aforementioned plunger moves beyond the predetermined position.

Preferably, the aforementioned locking means is provided to be capable of selecting a first position restraining rotation of the aforementioned rotary shaft and a second position liberating rotation of the aforementioned rotary shaft, and the aforementioned trigger device includes a detection mechanism for mechanically detecting a moving end of the aforementioned plunger, and a link mechanism setting the aforementioned locking device on the first position by the aforementioned detection mechanism when the aforementioned plunger moves beyond the predetermined position.

This structure makes detection of the position of the plunger implementable by the detection mechanism consisting of only a mechanical structure, whereby safety of the operation of the injector head can be attained regardless of a failure of electric control.

As a further preferable mode in the aforementioned mechanical locking mechanism and injector head, the aforementioned locking device includes a fixed lock ring provided around the aforementioned rotary shaft and including a groove portion having such a sliding surface that the distance between the sliding surface and the center of the aforementioned rotary shaft gradually shortens along a prescribed rotational direction of the aforementioned rotary shaft on a side facing the aforementioned rotary shaft, a lock pin arranged in the aforementioned groove portion and a movable lock ring holding the aforementioned lock pin to be movable between a first position locating the aforementioned lock pin between a surface of the aforementioned sliding surface most shortening the distance between the sliding surface and the aforementioned rotary shaft and the aforementioned rotary shaft and restraining rotation of the aforementioned rotary shaft by a wedge effect and a second position liberating rotation of the aforementioned rotary shaft in the aforementioned groove portion.

Further, the aforementioned detection mechanism includes a follower rotary shaft rotating following rotation of the aforementioned drive or the aforementioned motor, a body plate having the same rotation center as the rotation center of the aforementioned follower rotary shaft, a first gear having the same rotation center as the rotation center of the aforementioned follower rotary shaft, to which rotation of the aforementioned follower rotary shaft is transmitted through a first gear mechanism supported on the peripheral portion of the aforementioned body plate and a second gear having the same rotation center as the rotation center of the aforementioned follower rotary shaft, having a specific rotation control mechanism and arranged to be opposite to the aforementioned first gear, a surface of either one of the aforementioned first gear and the aforementioned second gear opposed to the other gear is provided with a pin projecting toward the other gear, a surface of the other gear opposed to one of the gears is provided with a ring-shaped guide slit having both end portions and extending along the rotation locus of the pin to be capable of receiving the aforementioned pin, and the aforementioned link mechanism has an engaging pin provided on the aforementioned movable lock ring, an operating mechanism provided to be rotatable about a prescribed axis for rotating the aforementioned movable lock ring so that the aforementioned lock pin is on the first position with an end engaging with aforementioned engaging pin and a link bar having an end coupled to the peripheral portion of the aforementioned body plate by a universal joint and another end coupled to the other end of the aforementioned operating mechanism by a universal joint.

Further, the aforementioned operating mechanism has an electric signal generator converting movement of the aforementioned operating mechanism to an electric signal.

In addition, the aforementioned trigger device has a device limiting the stroke of the aforementioned movable shaft or the aforementioned plunger.

BRIEF DESCRIPTION OF THE DRAWINGS

FIG. 4A is a front elevational view, and FIG. 4B is a plan view.

BEST MODE FOR CARRYING OUT THE INVENTION

A mechanical locking mechanism according to an embodiment based on the present invention is now described with reference to the case of applying this mechanism to a medical injector head. First, the structure of an injector head 1000 according to the embodiment based on the present invention is described with reference to FIG. 1.

Figure 1:
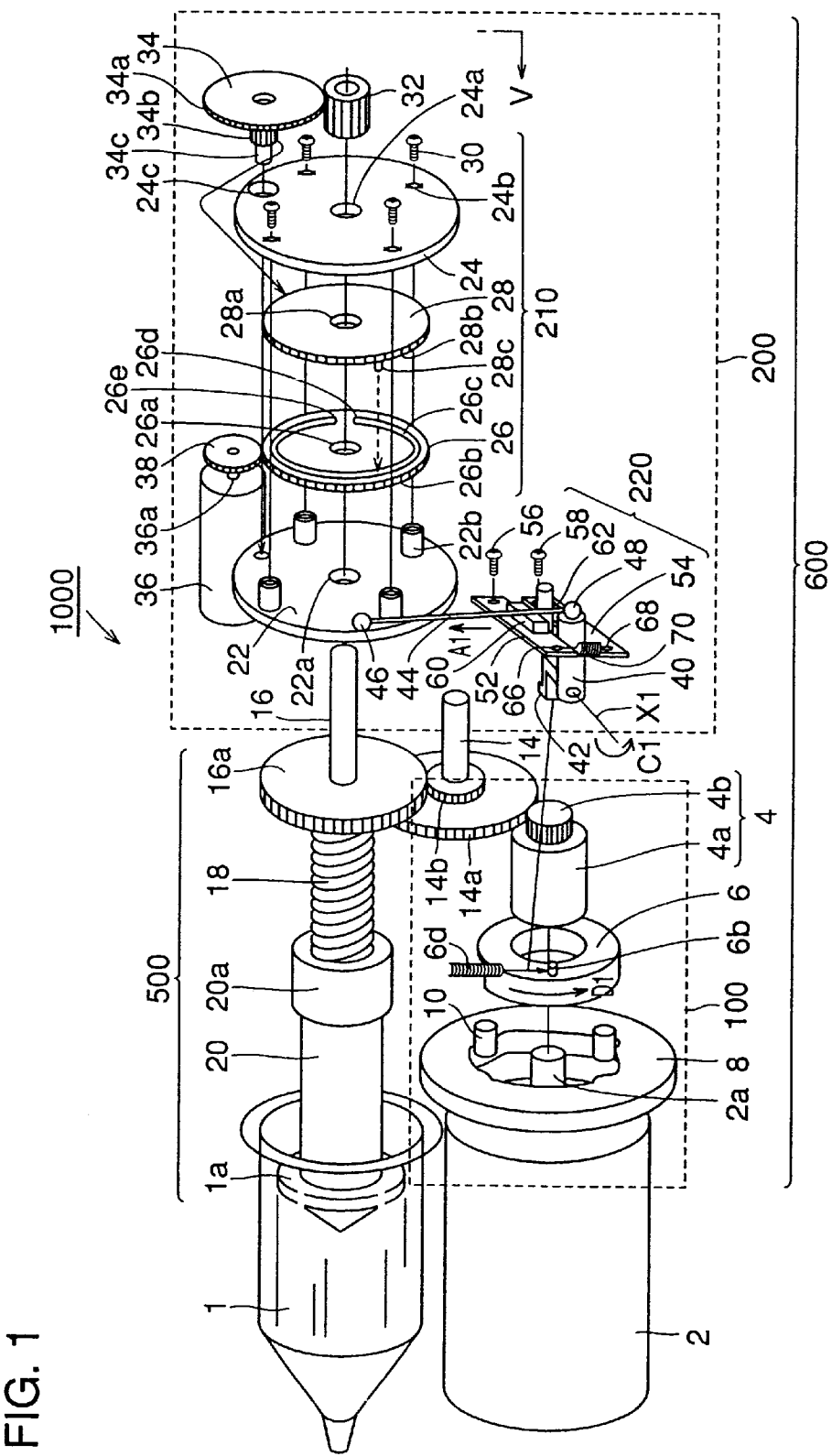
FIG. 1 is an exploded view showing a state decomposing principal components in order to clearly show the internal structure of an injector head in an embodiment based on the present invention.

FIG. 1 shows a state decomposing principal components while omitting illustration of a frame for supporting these principal components and a potentiometer for position control of a plunger etc. in order to clearly show the internal structure. It is assumed that a syringe 1 filled with a contrast medium therein is attached to this injector head 1000.

[Structure of Injector Head 1000]

The injector head 1000 according to this embodiment includes a plunger 20 as a movable shaft capable of reciprocating in a direction of movement of a piston la in the syringe 1, a plunger drive 500 for converting rotary motion of a plunger motor 2 as a drive to linear motion in order to supply this plunger 20 with reciprocation and a safety device 600 as safety means for restraining rotation of a rotary shaft 2a of the plunger motor 2 by a mechanical operation when the plunger 20 moves beyond a predetermined position.

[1] Plunger Drive 500

A pinion 4 is mounted on the rotary shaft 2a of the plunger motor 2. The pinion 4 has a body portion 4a and a pinion gear 4b, and the rotary shaft 2a engages with the body portion 4a. Preferably, a coupling structure readily separated from the rotary shaft 2a and capable of absorbing external impact is employed for the body portion 4a.

Rotation of the rotary shaft 2a of the plunger motor 2 is transmitted by a gear train consisting of the pinion gear 4b, a gear (large) 14a and a gear (small) 14b mounted on a rotary shaft 14 and a gear 16a mounted on a follower rotary shaft 16 to a ball screw 18. A plunger base 20a provided with a screw on its inner peripheral surface meshes with the ball screw 18. Rotary motion of the plunger motor 2 is converted to linear motion of the plunger 20 due to the aforementioned structure.

[2] Safety Device 600

The safety device 600 includes a locking device 100 provided on the rotary shaft 2a to be capable of restraining rotation of the rotary shaft 2a of the plunger motor 2 and a trigger device 200 mechanically operating the locking device 100 so that the locking device 100 restrains the rotary shaft 2a when the plunger 20 moves beyond a predetermined position.

(1) Specific Structure of Locking Device 100

Figure 2:
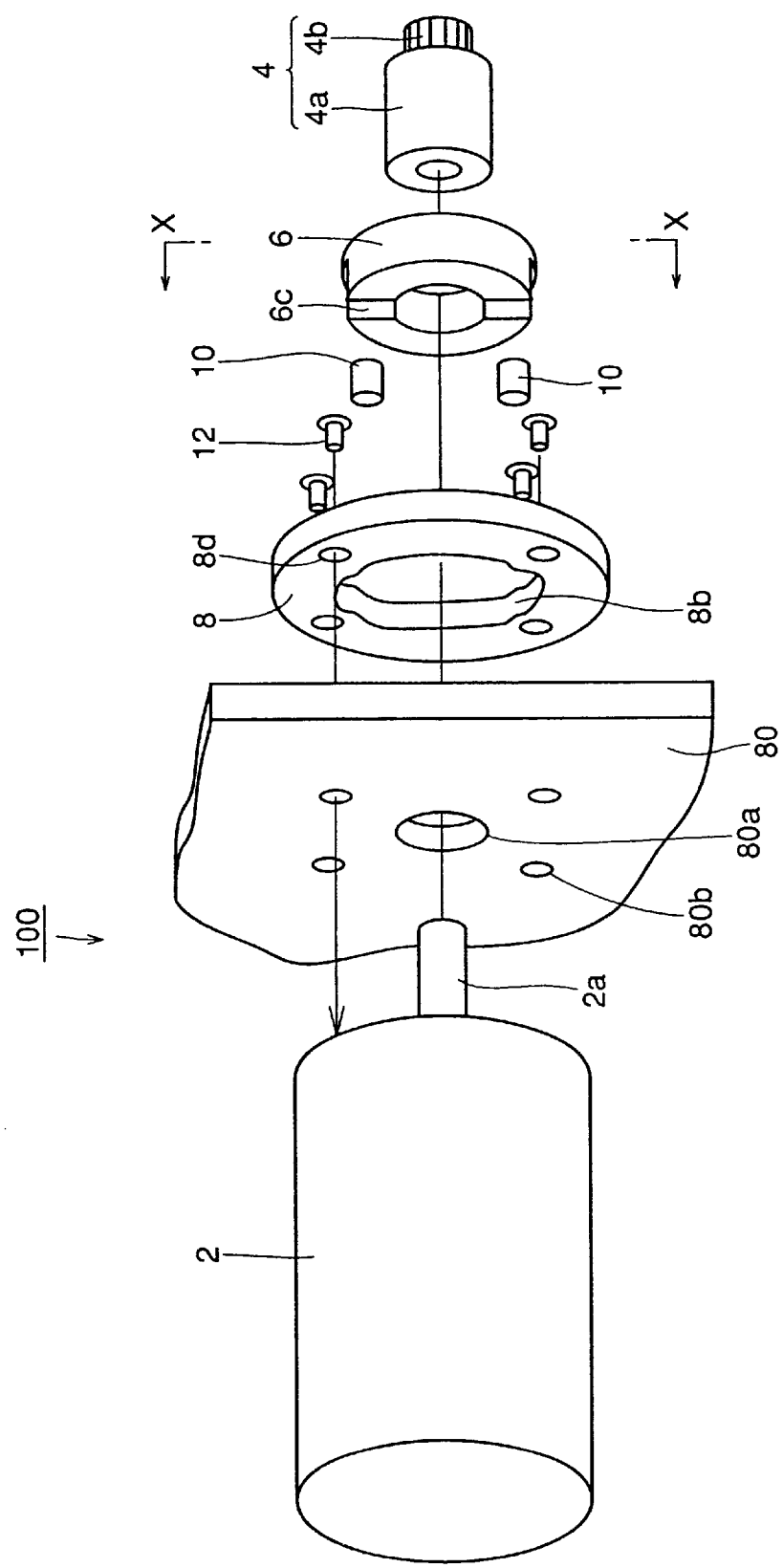
FIG. 2 is an exploded view for illustrating the structure of a locking device 100 according to a first embodiment based on the present invention.
Figure 3A:
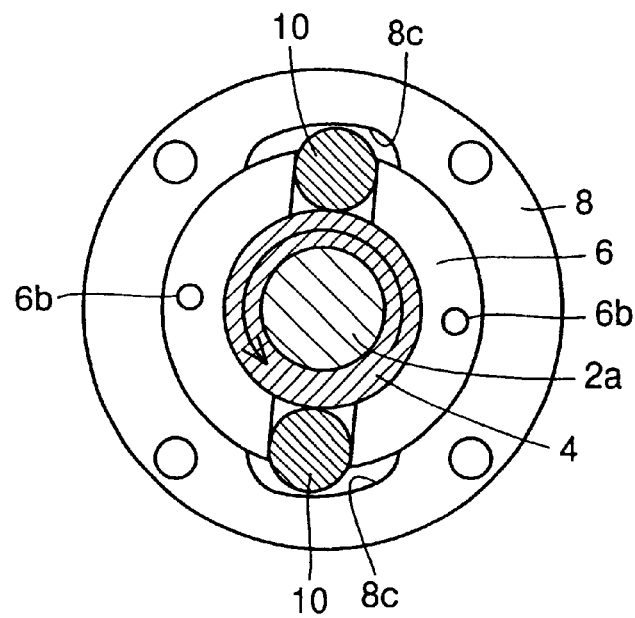
FIG. 3A and FIG. 3B are sectional views taken along the line X—X in FIG. 2 in a state assembling the locking device 100 according the first embodiment based on the present invention.
Figure 3B:
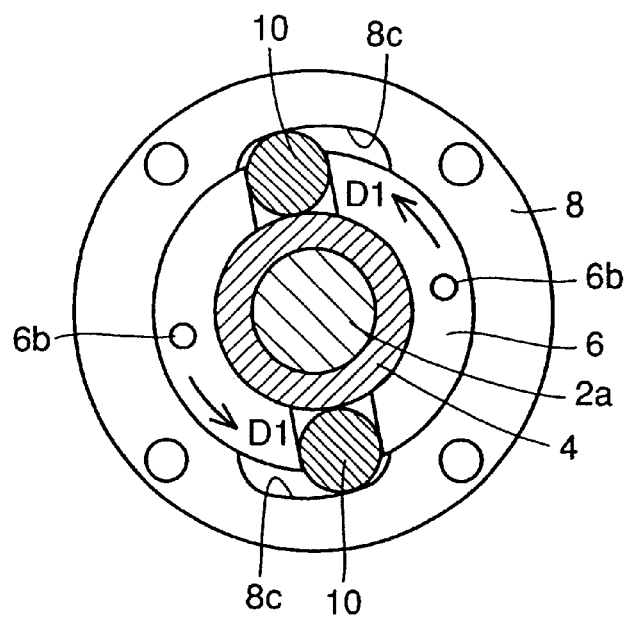

The specific structure of the locking device 100 is described with reference to FIG. 1, FIG. 2 and FIG. 3A and FIG. 3B. FIG. 2 is an exploded view for illustrating the structure of the locking device 100, and FIG. 3A and FIG. 3B are sectional views of a state assembling the locking device 100 taken along the line X—X in FIG. 2.

The body portion 4a of the pinion 4 is engaged with the rotary shaft 2a in such a state that the rotary shaft 2a of the plunger motor 2 is inserted in a rotary shaft hole 80a provided in a frame 80 (see FIG. 2). A movable lock ring 6 is rotatably arranged on the outer peripheral surface of the body portion 4a of the pinion 4.

A fixed lock ring 8 is arranged on the outer peripheral surface of the movable lock ring 6, and this fixed lock ring 8 is fixed to the frame 80 by fitting bolts 12 through mounting holes 8d provided on the fixed lock ring 8 and mounting holes 80b provided on the frame 80 (see FIG. 2). Lock pins 10 are stored between storage portions 6c (details are described later) of the movable lock ring 6 and concave portions 8b (details are described later) of the fixed lock ring 8.

The movable lock ring 6 is provided with a coil spring 6d for limiting rotation in a direction D1 in FIG. 1.

The movable lock ring 6, the fixed lock ring 8 and the lock pins 10 must satisfy precision and strength, and hence it is preferable to employ a material employed for bearings or the like such as a hardened steel product, for example.

Figure 4A:
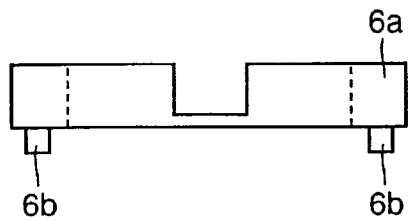
FIG. 4A and FIG. 4B are diagrams of a movable lock ring 6 of the injector head according to the embodiment based on the present invention.
Figure 4B:
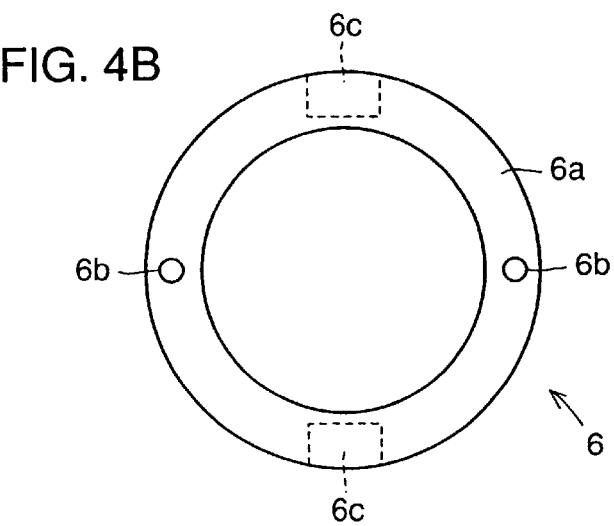

The detailed structure of the movable lock ring 6 is described with reference to FIG. 4A and FIG. 4B. FIG. 4A is a front elevational view of the movable lock ring 6, and FIG. 4B is a plan view of the movable lock ring 6. The movable lock ring 6 has a ring-shaped movable ring body 6a, engaging pins 6b provided on one surface side of the movable ring body 6a on positions opposed by 180° and the storage portions 6c provided on the other surface side of the movable ring body 6a on positions opposed by 180° and provided on positions deviating from the engaging pins 6b by 90°. The lock pins 10 are stored in these storage portions 6c, as described above.

Figure 5:
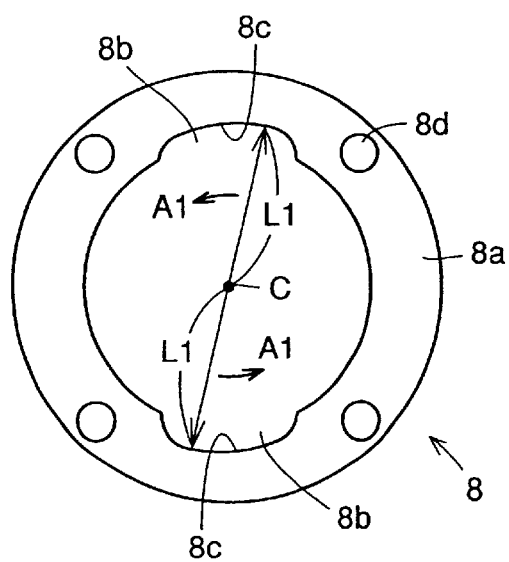
FIG. 5 is a front elevational view of a fixed lock ring 8 of the injector head according to the embodiment based on the present invention.

The detailed structure of the fixed lock ring 8 is described with reference to FIG. 5. FIG. 5 is a front elevational view of the fixed lock ring 8. The fixed lock ring 8 has a ring-shaped fixed ring body 8a, the concave portions 8b and the mounting holes 8d. The concave portions 8b have such sliding surfaces 8c that the distances (distances L1 in the figure) between the same and a rotary shaft center C gradually shorten along a prescribed rotational direction (direction of arrow A1 in the figure) of the rotary shaft 2a of the plunger motor 2.

In the locking device 100 consisting of the aforementioned structure, the state shown in FIG. 3A shows a position (second position) where the movable lock ring 6 liberates rotation of the pinion 4 and the rotary shaft 2a, and the state shown in FIG. 3B shows a position (first position) rotating the movable lock ring 6 in a direction of arrow D1 in the figure thereby locating the lock pins 10 between surfaces where the distances between the sliding surface 8c and the pinion 4 including the rotary shaft 2a most shorten and the pinion 4 and fixing rotation of the pinion 4 including the rotary shaft 2a by a wedge effect. Thus, it is structured to be capable of selecting the first position and the second position of the movable lock ring 6 by rotating the movable lock ring 6 with the engaging pins 6b.

(2) Specific Structure of Trigger Device 200

The specific structure of the trigger device 200 is described with reference to FIG. 1. The trigger device 200 includes a detection mechanism 210 for mechanically detecting a moving end of the plunger 20 and a link mechanism 220 setting the aforementioned locking device 100 on the first position by the detection mechanism 210 when the plunger 20 moves beyond a predetermined position.

(i) Specific Structure of Detection Mechanism 210

The specific structure of the detection mechanism 210 is described with reference to FIG. 1. Illustration of a potentiometer for position control of a stop plate 26 and a plunger plate 28 described later etc. is omitted. The follower rotary shaft 16 following rotation of the plunger motor 2 is provided.

A first body plate 22 and a second body plate 24 having the same rotation centers as the rotation center of this follower rotary shaft 16 are arranged with a prescribed space. The second body plate 24 is mounted on the first body plate 22 with fixing bolts 30 through mounting bosses 22b provided on the first body plate 22 and mounting holes 24b provided on the second body plate 24, so that the first body plate 22 and the second body plate 24 are integrally rotatable. The first body plate 22 is provided with an axial hole 22a while the second body plate 24 is provided with an axial hole 24a, and the follower rotary shaft 16 rotatably passes through this axial hole 22a and the axial hole 24a.

The plunger plate 28 as a first gear and the stop plate 26 as a second gear having the same rotation centers as the rotation center of the follower rotary shaft 16 are arranged between the first body plate 22 and the second body late 24. The plunger plate 28 is provided with an axial hole 28a while the stop plate 26 is provided with an axial hole 26a, and the follower rotary shaft 16 rotatably passes through this axial hole 28a and the axial hole 26a.

A gear 28b is provided around the plunger plate 28, and rotation of the follower rotary shaft 16 is transmitted to the plunger plate 28 through a first gear mechanism consisting of a pinion 32 and a satellite gear 34. The satellite gear 34 has a gear 34a meshing with the pinion 32, a gear 34b meshing with the gear 28b and a rotary shaft 34c supporting the gear 34a and the gear 34b. The satellite gear 34 is supported by the first body plate 22 and an axial hole 24c provided on the peripheral portion of the second body plate 24 to be rotatable about the rotary shaft 34c.

A plunger pin 28c projecting toward the second gear 26 is provided on a surface of the plunger plate 28 opposed to the stop plate 26. A ring-shaped guide slot 26c having a first end portion 26d and a second end portion 26e and extending along the rotation locus of the plunger pin 28c is provided on a surface of the stop plate 26 opposed to the plunger plate 28 to be capable of receiving the plunger pin 28c.

A gear 26b is provided on the periphery of the stop plate 26, and it has a mechanical motor 36 and a control gear 38 mounted on a rotary shaft 36a of this mechanical motor 36 for meshing with the gear 26b as a rotation control mechanism for the stop plate 26. It is preferable to employ a geared motor, in order to let the mechanical motor 36 also have a role of inhibiting rotation of the stop plate 26.

While the plunger pin 28c is provided on the aforementioned plunger plate 28 and the guide slit 26c is provided on the stop plate 26, it is also possible to provide the guide slit 26c on the plunger plate 28 and provide the plunger pin 28c on the stop plate 26. Further, it is also possible to replace the guide slit 26c with the plunger pin 28c.

(ii) Specific Structure of Link Mechanism 220

Figure 6:
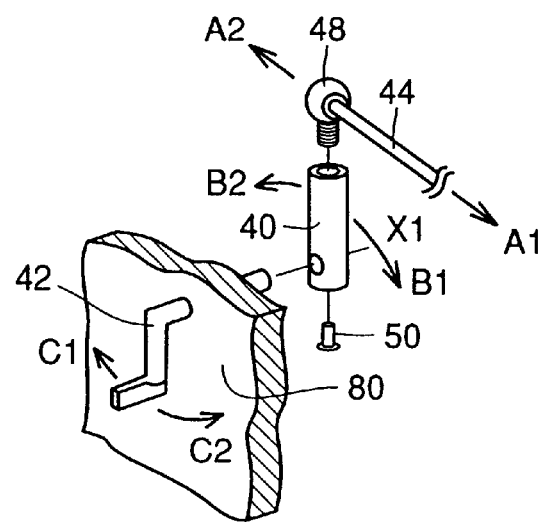
FIG. 6 is a perspective view showing the structure of an operating mechanism of the injector head according to the embodiment based on the present invention.

The specific structure of the link mechanism 220 is described with reference to FIG. 1 and FIG. 6. FIG. 6 is a perspective view showing the structure of an operating mechanism (described later).

A kick plate 42 engaging with the engaging pins 6b provided on the aforementioned movable lock ring 6 and a link pin 40 supporting this kick plate 42 on an end with a screw 50 are mounted on the frame 80 to be rotatable about an axis X1 (see FIG. 1).

Another other end of a link bar 44 is coupled to the other end of the link pin 40 by a universal joint 48. As shown in FIG. 6, the link pin 40 rotates in a direction B1 about the axis X1 while the kick plate 42 rotates in a direction C1 about the axis X1 when the link bar 44 moves in a direction A1. When the link bar 44 moves in a direction A2, the link pin 40 rotates in a direction B2 about the axis X1 while the kick plate 42 rotates in a direction C2 about the axis X1.

On the other hand, one end of the link bar 44 is mounted on the peripheral portion of the first body plate 22 by a universal joint 46. The universal joints 46 and 48 are employed for coupling the link bar 44 since the first body plate 22 rotates and hence joints having small plays are required due to the necessity for correctly transmitting movement of the first body plate 22 to the link mechanism 220.

In the link mechanism 220 consisting of the aforementioned structure, the kick plate 42 rotates in the direction C1 about the axis X1 when the link bar 44 is pulled up in the direction A1 by the first body plate 2 with reference to FIG. 1. Thus, the movable lock ring 6 rotates in a direction D1, and the lock pin 10 reaches the first position.

Figure 7:
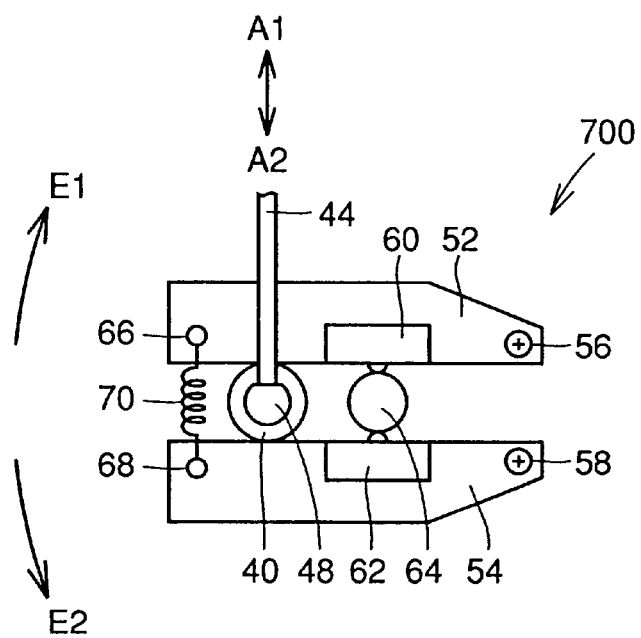
FIG. 7 is a front elevational view showing a schematic structure of an electric signal conversion mechanism 700 of the injector head according to the embodiment based on the present invention.

In this embodiment, an electric signal conversion mechanism 700 for extracting the operation of the link mechanism 220 as an electrical signal is employed. This electric signal conversion mechanism 700 is now described with reference to FIG. 1 and FIG. 7. FIG. 7 is a front elevational view showing a schematic structure of the electric signal conversion mechanism 700.

Switch plates 52 and 54 are provided to hold the link pin 40 from above and from below. A coil spring 70 is mounted on single ends of the switch plates 52 and 54 with screws 66 and 68. Other ends of the switch plates 52 and 54 are mounted with respect to the frame (not shown) with screws 56 and 58 respectively about the screws 56 and 58. Therefore, the switch plate 52 is rotatable in a direction E1 in the figure, and the switch plate 54 is rotatable in a direction E2 in the figure.

Microswitches 60 and 62 are mounted on the respective ones of the switch plates 52 and 54 in a state in contact with the link pin 40 in a general state. Either type of microswitches generating ON signals in the state in contact with the link pin 40 or generating ON signals in a state separate from the link pin 40 may be employed for the microswitches 60 and 62.

The kick plate 42 is not directly coupled to the movable lock ring 6 but set in the state engaging with the engaging pins 6b provided on the movable lock ring 6, in order to avoid application of impact to the kick plate 42 when large force is applied to the movable lock ring 6.

[Operation of Injector Head 1000]

Operations of the injector head 1000 consisting of the aforementioned structure are now described with reference to FIG. 8 to FIG. 16. FIG. 8, FIG. 10, FIG. 11, FIG. 12 and FIG. 14 are diagrams typically showing the detection mechanism 210 corresponding to views along a line V in FIG. 1. For convenience of illustration, the plunger plate 28 is shown with two-dot chain lines, and illustration of the second body plate 24 is omitted.

Figure 8:
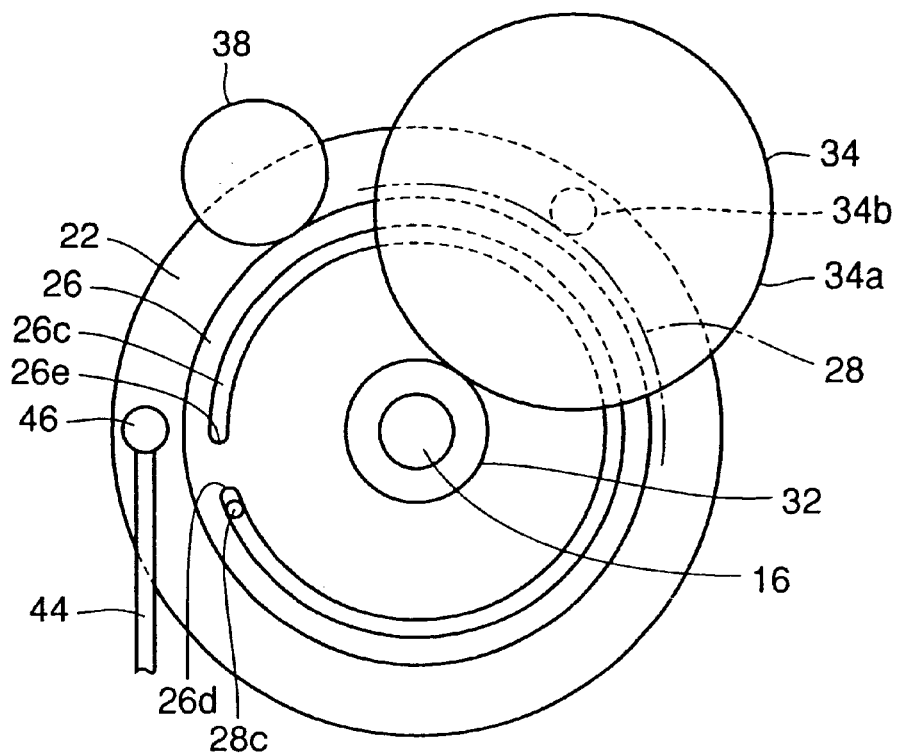
FIG. 8 is a first diagram typically showing operations of a detection mechanism 210 corresponding to a view along arrow V in FIG. 1.
Figure 9:
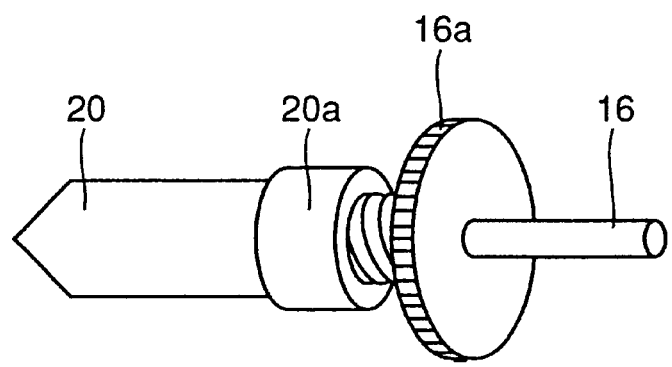
FIG. 9 is a model diagram for illustrating the position of a plunger 20 in the state of FIG. 8.
Figure 12:
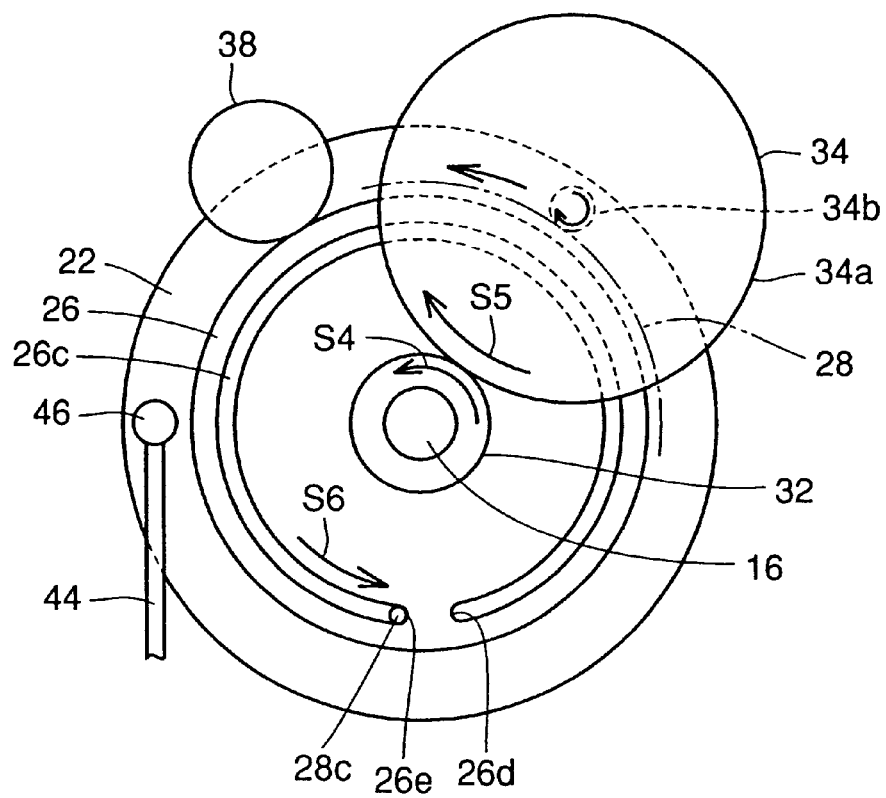
FIG. 12 is a fourth diagram typically showing operations of the detection mechanism 210 corresponding to the view along arrow V in FIG. 1.
Figure 13:
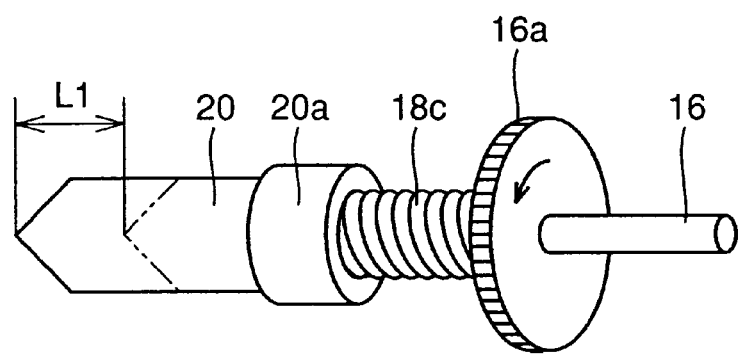
FIG. 13 is a model diagram for illustrating the position of the plunger 20 in the state shown in FIG. 12.
Figure 14:
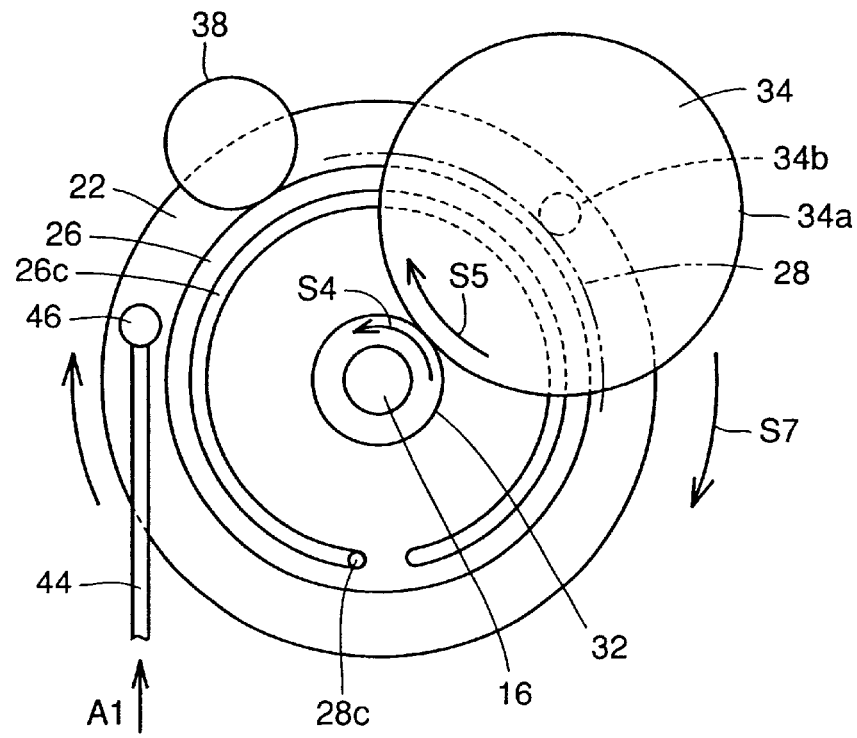
FIG. 14 is a fifth diagram typically showing operations of the detection mechanism 210 corresponding to the view along arrow V in FIG. 1.
Figure 15A:
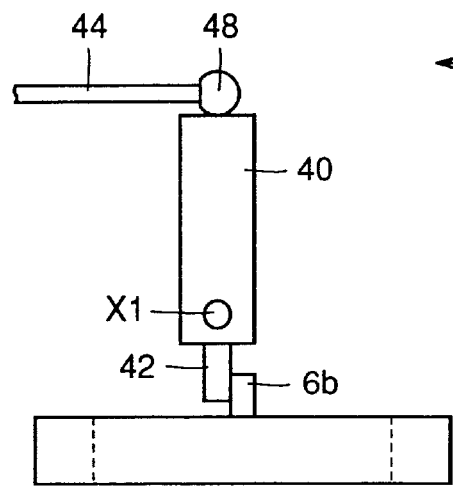
FIGS. 15A and 15B are fifth diagrams typically showing operations of the detection mechanism 210 corresponding to the view along arrow V in FIG. 1.
Figure 15B:
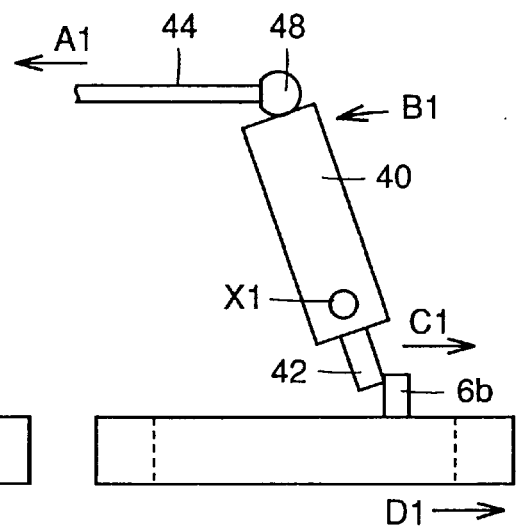
Figure 16:
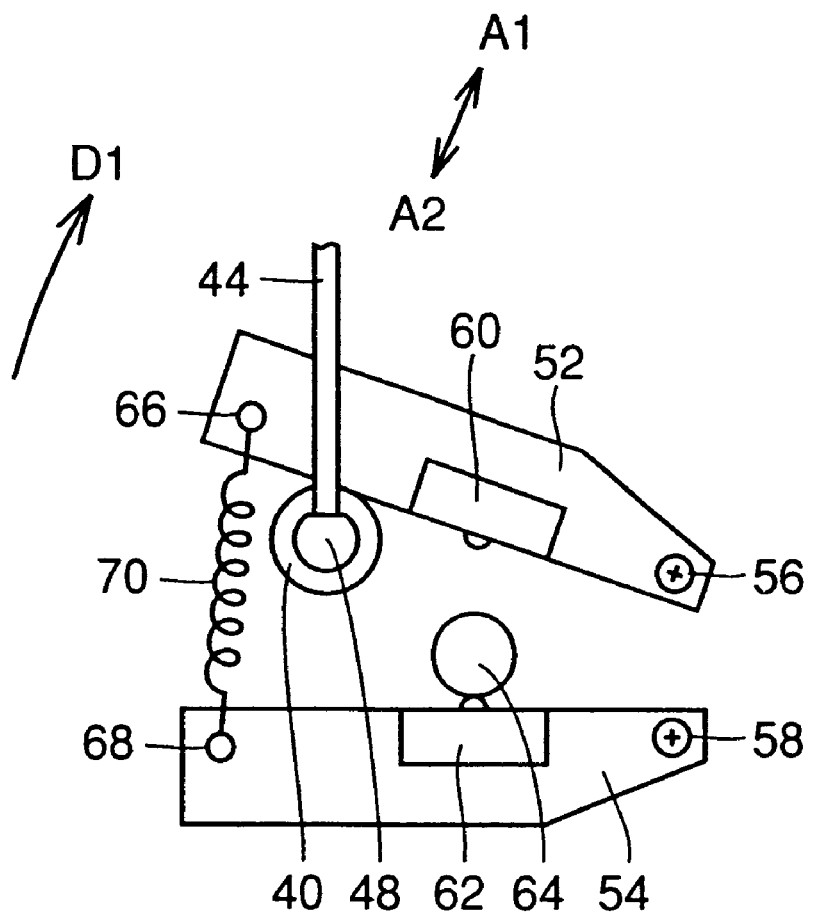
FIG. 16 is a model diagram showing operations of the electric signal conversion mechanism 700.

FIG. 9 is a model diagram for illustrating the position of the plunger 20 in the state of FIG. 8, and FIG. 13 is a model diagram for illustrating the position of the plunger 20 in the state of FIG. 12. FIG. 15A and FIG. 15B are model diagrams for illustrating operations of the link mechanism 220 in the state of FIG. 14, and FIG. 16 is a diagram showing the state of the electric signal conversion mechanism 700 in the state of FIG. 14.

First, FIG. 8 and FIG. 9 show an initial state position of the plunger 20. On this initial state position, the plunger 20 is on a position most approximate to the gear 16a, and the end 26d of the guide slit 26c provided on the stop plate 26 is located on the position of the plunger pin 28c provided on the plunger plate 28.

Figure 10:
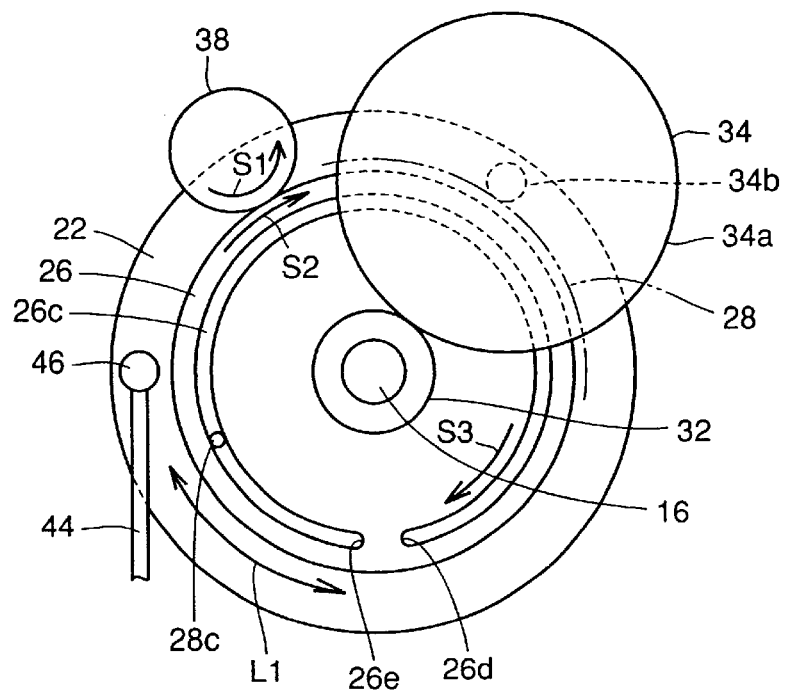
FIG. 10 is a second diagram typically showing operations of the detection mechanism 210 corresponding to the view along arrow V in FIG. 1.

Referring to FIG. 10, the quantity of movement of the plunger 20 is then decided. There is proportionate relation between the injection rate of the contrast medium by movement of the plunger 20 and the circular arc length of the guide slit 26c. When selecting L1 (mm) as the circular arc length corresponding to the injection rate of the contract medium by movement of the plunger 20, the mechanical motor 36 and the control gear 38 are rotated in a direction S1 and the stop plate 26 is rotated in a direction S2 for setting the circular arc distance between the other end 26e of the guide slit 26c and the plunger pin 28c to reach L1+α (mm). α(mm) indicates a circular arc length corresponding to an allowable quantity which may be exceeded by the injection rate of the contrast medium, and the value of α(mm) is so set that the allowable quantity is 1 to 2 (ml).

Figure 11:
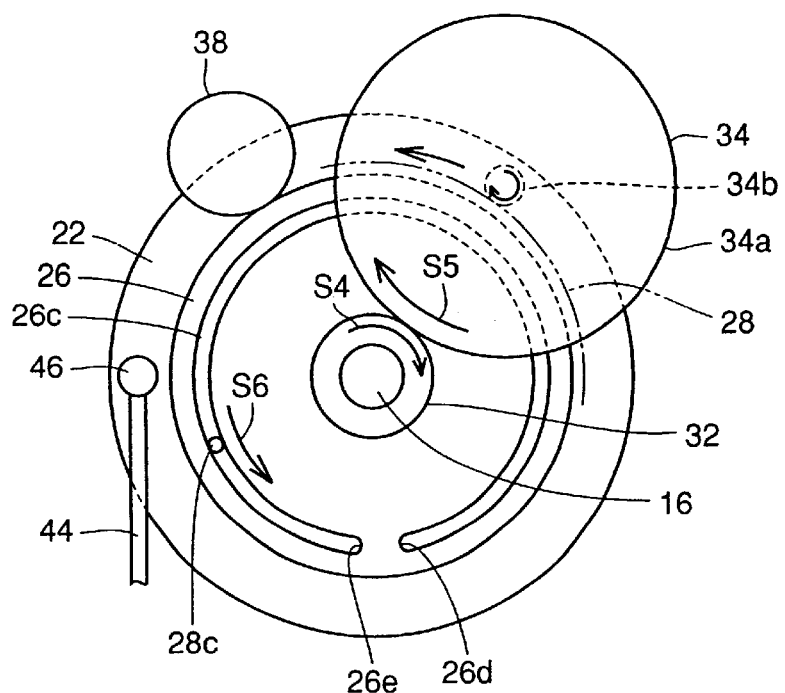
FIG. 11 is a third diagram typically showing operations of the detection mechanism 210 corresponding to the view along arrow V in FIG. 1.

Referring to FIG. 11, the plunger motor 2 is rotated in a direction S4 for rotating the pinion 32 in the direction S4 in a state stopping the mechanical motor 36 and fixing the stop plate 26. Thus, the satellite gear 34 rotates in a direction S5 and the plunger plate 28 rotates in a direction S6, whereby the plunger pin 28c moves toward the other end 26e of the guide slit 26c.

Referring to FIG. 12, the plunger 20 advances L1 as shown in FIG. 13 in such a state that the plunger pin 28c is in contact with the other end 26e of the guide slit 26c. The plunger pin 28c, going to further move due to rotation of the plunger motor 2, cannot move since the plunger pin 28c is in contact with the other end 26e of the guide slit 26c. Referring to FIG. 14, rotation of the plunger plate 28 stops since the plunger pin 28c cannot move.

Thus, rotational force of the plunger motor 2 is converted to force rotating the satellite gear 34 in a direction S7 along the gear 28b provided on the plunger plate 28. The satellite gear 34 is supported by the first body plate 22 and the second body plate 24, and hence the first body pale 22 and the second body plate 24 also rotate in the direction S7 along with the satellite gear 34. Consequently, it follows that the link bar 44 coupled to the first body plate 22 is pulled up in the direction A1.

When the link bar 44 is pulled up in the direction A1, the link pin 40 rotates in the direction B1 about the axis X1 and the link bar 44 rotates in the direction C1, as shown in FIG. 15A and FIG. 15B. Thus, the engaging pins 6b rotate in the direction D1 and the lock pins 10 held by the movable lock ring 6 reach the first position shown in FIG. 3B, to mechanically restrain the rotary shaft 2a and the pinion 4 by the wedge effect. Thus, it follows that the safety device 600 according to this embodiment operates.

While the plunger 20 is originally controlled to automatically stop at a previously set injection rate, the aforementioned electric signal conversion mechanism 700 performs control of restraining rotation of the plunger motor 2 if it does not stop.

More specifically, the link bar 44 is pulled up in the direction A1 and the switch plate 52 is raised up by the link pin 40 as shown in FIG. 16 when the plunger 20 progresses without stopping. Consequently, the microswitch 60 enters an OFF state, is converted to a prescribed electric signal and performs control of restraining rotation of the plunger motor 2. Therefore, the safety device 600 is employed as a backup in the case where electrical control fails.

Thus, in the injector head 1000 according to this embodiment, torque caused on the rotary shaft 2a of the plunger motor 2 is smaller than torque caused on the plunger 20, whereby it is possible to stop movement of the plunger 20 with small force by restraining rotation of the rotary shaft 2a of the plunger motor 2 by a mechanical operation. Therefore, stress applied to the components forming the safety device 600 also reduces, and it is possible to attain miniaturization of these components and following miniaturization of the injector head 1000.

As hereinabove described, adjustment of the quantity of movement of the plunger 20 and detection of the position of the plunger 20 are rendered implementable by the detection mechanism 210 consisting of only a mechanical structure, whereby safety of the operations of the injector head 1000 can be attained regardless of failure of electric control.

In addition, it is possible to more readily perform maintenance than the conventional injector head by unifying the trigger device 200 including a number of gears in the aforementioned injector head 1000 as a gearbox.

Further, it is possible to readily visually confirm the positions of the plunger pin 28c and the guide slit 26c from the side of the first body pale 22 by forming the first body plate 22 and the plunger plate 28 by transparent members.

While the case of application to an injector head employed for medical use has been described in the above embodiment, the functions/effects of the present invention are attained when applied to a device related to an object of preventing overrun of an apparatus. Further, it is possible to apply the present invention not only to the medical apparatus but also as a safety device for an apparatus such as a vehicle of an amusement park or the like particularly influencing human life.

The locking device 100, the trigger device 200, the detection device 300, the link mechanism 400, the plunger drive mechanism 500, the safety device 600 and other structures in the embodiment disclosed this time are illustrative in all points and not restricted to the aforementioned embodiment. The technical scope of the present invention is not decided by the aforementioned embodiment but decided by the aforementioned scope of claim for patent, and it is intended that all modifications within the meaning and range equivalent to the scope of claim for patent are included.

According to the mechanical locking mechanism and the injector head based on the present invention, the torque caused on the rotary shaft of the drive or the motor is by far smaller than the torque caused on the movable shaft or the plunger, whereby it is possible to stop movement of the movable shaft or the plunger with small force by restraining rotation of the rotary shaft of the drive or the motor by a mechanical operation.

Therefore, stress applied to the components forming the safety device also reduces, and it is possible to attain miniaturization of these components and following miniaturization of the mechanical locking mechanism and the injector head. Further, detection of the position of the movable shaft or the plunger is rendered implementable by the detection mechanism consisting of only the mechanical structure, whereby safety of operations of the mechanical locking mechanism and the injector head can be attained regardless of failure of electrical control.

What is claimed is:

1. A mechanical locking mechanism comprising:
   a drive having a rotary shaft;
   a moveable shaft capable of linear motion;
   movable shaft drive means for converting rotary motion of the drive to motion of a prescribed direction in order to supply linear motion to said movable shaft; and
   safety means for restraining rotation of the rotary shaft of said drive by a mechanical operation when said movable shaft moves beyond a predetermined position;
   wherein said safety means includes a locking means provided in the vicinity of said rotary shaft to be capable of restraining rotation of the rotary shaft, said locking means configured to be capable of selecting
      a first position fixing rotation of said rotary shaft irrespective of a position of said movable shaft and
      a second position liberating rotation of said rotary shaft;
   wherein said safety means includes a trigger means mechanically operating said locking means so that said locking means restrains said rotary shaft when said movable shaft moves beyond the predetermined position;
   wherein said trigger means includes a detection mechanism for mechanically detecting a moving end of said movable shaft, and a link mechanism setting said locking means on the first position by said detection mechanism when said movable shaft moves beyond the predetermined position; and
   wherein said locking means includes:
      a fixed lock ring provided around said rotary shaft and including a groove portion having such a sliding surface that the distance between said sliding surface and the center of said rotary shaft gradually shortens along a prescribed rotational direction of said rotary shaft on a side facing said rotary shaft,
      a lock pin arranged in said groove portion, and
      a movable lock ring holding said lock pin to be movable between a first position locating said lock pin between a surface of said sliding surface most shortening the distance between said sliding surface and said rotary shaft and restraining rotation of said rotary shaft by a wedge effect and a second position liberating rotation of said rotary shaft in said groove portion.

2. A mechanical locking mechanism comprising:

a drive having a rotary shaft;

a moveable shaft capable of linear motion;

movable shaft drive means for converting rotary motion of the drive to motion of a prescribed direction in order to supply linear motion to said movable shaft; and safety means for restraining rotation of the rotary shaft of said drive by a mechanical operation when said movable shaft moves beyond a predetermined position;

wherein said safety means includes a locking means provided in the vicinity of said rotary shaft to be capable of restraining rotation of the rotary shaft, said locking means configured to be capable of selecting
a first position fixing rotation of said rotary shaft irrespective of a position of said movable shaft and
a second position liberating rotation of said rotary shaft;

wherein said safety means includes a trigger means mechanically operating said locking means so that said locking means restrains said rotary shaft when said movable shaft moves beyond the predetermined position;

wherein said trigger means includes a detection mechanism for mechanically detecting a moving end of said movable shaft, and a link mechanism setting said locking means on the first position by said detection mechanism when said movable shaft moves beyond the predetermined position; and wherein said detection mechanism includes:
a follower rotary shaft following rotation of said drive,
a body plate having the same rotation center as the rotation center of said follower rotary shaft,
a first gear, having the same rotation center as the rotation center of said follower rotary shaft, to which rotation of said follower rotary shaft is transmitted through a first gear mechanism supported on the peripheral portion of said body plate, and
a second gear having the same rotation center as the rotation center of said follower rotary shaft, having a specific rotation control mechanism and arranged to be opposite to said first gear,
a surface of either one of said first gear and said second gear opposed to the other gear is provided with a pin projecting toward the other gear and a surface of the other gear opposed to one of the gears is provided with a ring-shaped guide slit having both end portions extending along the rotation locus of the pin to be capable of receiving said pin, and
said link mechanism has:
an engaging pin provided on a movable lock ring,
an operating mechanism provided to be rotatable about a prescribed axis for rotating said movable lock ring so that said lock pin is in the first position and engaging with said engaging pin, and
a link bar having an end coupled to the peripheral portion of said body plate by a universal joint and another end coupled to the other end of said operating mechanism by a universal joint.

3. The mechanical locking mechanism according to claim 2, wherein
said operating mechanism has electric signal generation means converting movement of said operating mechanism to an electric signal.

4. A mechanical locking mechanism comprising:

a drive having a rotary shaft;

a fixed lock ring provided around said rotary shaft and capable of restraining a moveable shaft capable of linear motion and capable of restraining rotation of the rotary shaft;

movable shaft drive means for converting rotary motion of the drive to motion of a prescribed direction in order to supply linear motion to said movable shaft; and safety means for restraining rotation of the rotary shaft of said drive by a mechanical operation when said movable shaft moves beyond a predetermined position, wherein said safety means includes a said fixed lock ring;

wherein said safety means further includes a trigger means mechanically operating said locking means so that said locking means restrains said rotary shaft when said movable shaft moves beyond the predetermined position;

wherein said locking means is provided to be capable of selecting a first position fixing rotation of said rotary shaft and a second position liberating rotation of said rotary shaft, and said trigger means includes:
a detection mechanism for mechanically detecting a moving end of said movable shaft, and
a link mechanism setting said locking means on the first position by said detection mechanism when said movable shaft moves beyond the predetermined position; and
wherein said detection mechanism includes:
a follower rotary shaft following rotation of said drive,
a body plate having the same rotation center as the rotation center of said follower rotary shaft,
a first gear, having the same rotation center as the rotation center of said follower rotary shaft, to which rotation of said follower rotary shaft is transmitted through a first gear mechanism supported on the peripheral portion of said body plate, and
a second gear having the same rotation center as the rotation center of said follower rotary shaft, having a specific rotation control mechanism and arranged to be opposite to said first gear,
a surface of either one of said first gear and said second gear opposed to the other gear is provided with a pin projecting toward the other gear and a surface of the other gear opposed to one of the gears is provided with a ring-shaped guide slit having both end portions extending along the rotation locus of the pin to be capable of receiving said pin, and
said link mechanism has:
an engaging pin provided on a movable lock ring,
an operating mechanism provided to be rotatable about a prescribed axis for rotating said movable lock ring so that said lock pin is in the first position and engaging with said engaging pin, and
a link bar having an end coupled to the peripheral portion of said body plate by a universal joint and another end coupled to the other end of said operating mechanism by a universal joint.

5. The mechanical locking mechanism according to claim 4, wherein said operating mechanism has electric signal generation means converting movement of said operating mechanism to an electric signal.

6. A mechanical locking mechanism, comprising:

a drive having a rotary shaft;

a fixed lock ring provided around said rotary shaft capable of restraining a moveable shaft capable of linear motion;

movable shaft drive means for converting rotary motion of the drive to motion of a prescribed direction in order to supply linear motion to said movable shaft; and safety means for restraining rotation of the rotary shaft of said drive by a mechanical operation when said movable shaft moves beyond a predetermined position, wherein said safety means includes:

said fixed lock ring including a groove portion having such a sliding surface that the distance between said sliding surface and the center of said rotary shaft gradually shortens along a prescribed rotational direction of said rotary shaft on a side facing said rotary shaft, a lock pin arranged in said groove portion, and a movable lock ring holding said lock pin to be movable between a first position locating said lock pin between a surface of said sliding surface most shortening the distance between said sliding surface and said rotary shaft and restraining rotation of said rotary shaft by a wedge effect and a second position liberating rotation of said rotary shaft in said groove portion.

7. The mechanical locking mechanism according to claim 6, wherein said safety means further includes a trigger means mechanically operating said locking means so that said locking means restrains said rotary shaft when said movable shaft moves beyond the predetermined position.

8. The mechanical locking mechanism according to claim 7, wherein said locking means is provided to be capable of selecting a first position fixing rotation of said rotary shaft and a second position liberating rotation of said rotary shaft, and said trigger means includes:

a detection mechanism for mechanically detecting a moving end of said movable shaft, and a link mechanism setting said locking means on the first position by said detection mechanism when said movable shaft moves beyond the predetermined position.

9. The mechanical locking mechanism according to claim 6, wherein said detection means has means limiting the stroke of said movable shaft.

* * * * *